United States Patent
Damadian et al.

(10) Patent No.: US 7,680,525 B1
(45) Date of Patent: Mar. 16, 2010

(54) METHOD FOR LATERAL MOTION MAGNETIC RESONANCE IMAGING

(75) Inventors: Raymond V. Damadian, Woodbury, NY (US); Rajendra Shenoy, Dix Hills, NY (US); Jevan Damadian, East Northport, NY (US)

(73) Assignee: Fonar Corporation, Melville, NY (US)

( * ) Notice: Subject to any disclaimer, the term of this patent is extended or adjusted under 35 U.S.C. 154(b) by 1003 days.

(21) Appl. No.: 10/304,582

(22) Filed: Nov. 26, 2002

Related U.S. Application Data

(60) Provisional application No. 60/333,384, filed on Nov. 26, 2001, provisional application No. 60/370,677, filed on Apr. 8, 2002.

(51) Int. Cl.
*A61B 5/05* (2006.01)

(52) U.S. Cl. .................. 600/415; 324/318; 324/322; 600/421

(58) Field of Classification Search ......... 600/407–408, 600/410–423; 324/306–309, 318–322; 5/601; 378/17, 20, 68, 69
See application file for complete search history.

(56) References Cited

U.S. PATENT DOCUMENTS

| | | | |
|---|---|---|---|
| 4,534,358 A | | 8/1985 | Young |
| 4,924,198 A | | 5/1990 | Laskaris |
| 5,008,624 A | | 4/1991 | Yoshida |
| 5,153,546 A | * | 10/1992 | Laskaris ............ 335/216 |
| 5,349,956 A | * | 9/1994 | Bonutti ............ 600/425 |
| 5,520,181 A | | 5/1996 | Kreidler et al. |
| 5,592,090 A | | 1/1997 | Pissanetzky |
| 5,640,958 A | | 6/1997 | Bonutti |
| 5,680,861 A | * | 10/1997 | Rohling ............ 600/407 |
| 5,735,278 A | * | 4/1998 | Hoult et al. ........ 600/422 |
| 5,779,637 A | * | 7/1998 | Palkovich et al. ...... 600/415 |
| 5,899,859 A | * | 5/1999 | Votruba et al. ........ 600/415 |
| 6,075,364 A | * | 6/2000 | Damadian et al. ...... 324/319 |
| 6,246,239 B1 | * | 6/2001 | Krogmann et al. ..... 324/318 |
| 6,335,623 B1 | * | 1/2002 | Damadian et al. ...... 324/320 |
| 6,414,490 B1 | | 7/2002 | Damadian et al. |

(Continued)

FOREIGN PATENT DOCUMENTS

JP 1-042056 9/1989

OTHER PUBLICATIONS

Karhu JO, Parkkola RK, Kamu ME, Kormano MJ, Koskinen SK. Kinematic magnetic resonance imaging of the upper cervical spine using a novel position device. Oct. 1999. Lippincot, Williams, & Wilkins. 24(19):2046-56.*

(Continued)

*Primary Examiner*—Brian Casler
*Assistant Examiner*—Amanda Lauritzen
(74) *Attorney, Agent, or Firm*—Lerner, David, Littenberg, Krumholz & Mentlik, LLP

(57) ABSTRACT

The method includes positioning a patient within a receiving space of a stand-up MRI apparatus and imaging the region of interest of the patient while the patient moves the region of interest. Further in accordance with the method the patient may be positioned such that the patient faces a pole face of a magnet of the MRI apparatus. The apparatus comprises a patient support which allows imaging of a patient's spine with a gravitational load on the spinal system.

21 Claims, 9 Drawing Sheets

U.S. PATENT DOCUMENTS

| | | | |
|---|---|---|---|
| 6,677,753 B1 * | 1/2004 | Danby et al. | 324/318 |
| 6,806,712 B2 * | 10/2004 | Akgun | 324/318 |
| 6,828,792 B1 * | 12/2004 | Danby et al. | 324/318 |
| 7,123,008 B1 * | 10/2006 | Damadian et al. | 324/309 |
| 7,230,424 B1 * | 6/2007 | Morrone | 324/309 |
| 2003/0204136 A1 * | 10/2003 | Green et al. | 600/415 |
| 2005/0187459 A1 * | 8/2005 | Trequattrini et al. | 600/415 |

OTHER PUBLICATIONS

Hodge et al. Dynamic MR Imaging and Stress Testing in Glenohumeral Instability: Comparison With Normal Shoulders and Clinical/Surgical Findings. Journal of Magnetic Resonance Imaging 13:748-756 (2001).*

U.S. Appl. No. 08/978,084, filed Nov. 25, 1997, (now abondoned).

U.S. Appl. No. 09/718,946, filed Nov. 22, 2000.

U.S. Appl. No. 10/126,015, filed Apr. 18, 2002.

John F. Schenck, MD, PhD., et als. "Superconducting Open-Configuration MR Imaging System for Image-guided Therapy[1]," Interventional Radiology, Jun. 1995, pp. 805-814.

U.S. Appl. No. 10/126,015 filed Apr. 18, 2002.

U.S. Appl. No. 09/718,946 filed Nov. 22, 2000.

U.S. Appl. No. 08/978,084 filed Nov. 27, 1997 (now abandoned).

* cited by examiner

METHOD FOR LATERAL MOTION MAGNETIC RESONANCE IMAGING

CROSS-REFERENCE TO RELATED APPLICATIONS

The present application claims the benefit of U.S. Provisional Application No. 60/333,384, filed Nov. 26, 2001 and entitled "METHOD AND APPARATUS FOR MAGNETIC RESONANCE IMAGING," and U.S. Provisional Application No. 60/370,677, filed Apr. 8, 2002 and entitled "METHOD AND APPARATUS FOR MAGNETIC RESONANCE IMAGING," the disclosures of which are incorporated by reference herein in their entirety.

BACKGROUND OF THE INVENTION

The present invention relates to magnetic resonance imaging apparatus and procedures. In magnetic resonance imaging, an object to be imaged as, for example, a body of a human subject is exposed to a strong, substantially constant static magnetic field. Radio frequency excitation energy is applied to the body, and this energy causes the spin vectors of certain atomic nuclei within the body to rotate or "precess" around axes parallel to the direction of the static magnetic field. The precessing atomic nuclei emit weak radio frequency signals, referred to herein as magnetic resonance signals. Different tissues produce different signal characteristics. Tissue relaxation times are a major factor in determining signal strength. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. Also, magnetic resonance imaging can obtain images of soft tissues and other features within the body which are not readily visualized using other imaging techniques. Accordingly, magnetic resonance imaging has been widely adopted in the medical and allied arts.

Several factors impose significant physical constraints in positioning of patients and ancillary equipment in MRI imaging. Many MRI systems use solenoidal superconducting coils to provide the static magnetic field arranged so that the patient is disposed within a small tube running through the center of the coils. The coils and tube typically extend along a horizontal axis, so that the long axis or head-to-toe axis of the patient's body must be in a horizontal position during the procedure. Moreover, equipment of this type provides a claustrophobic environment for the patient. Iron core magnets have been built to provide a more open environment for the patient. These magnets typically have a ferromagnetic frame with a pair of ferromagnetic poles disposed one over the other along a vertical pole axis with a gap between them for receiving the patient. The frame includes ferromagnetic flux return members such as plates or columns that are located outside the patient receiving area and extend vertically. A magnetic field is provided by permanent magnets or electromagnetic coils (superconductive or resistive) associated with the frame. A magnet of this type can be designed to provide a more open environment for the patient. However, it is still generally required for the patient to lie with his or her long axis horizontal.

Recently, ferromagnetic frame magnets having horizontal pole axes have been developed. As disclosed, for example, in copending, commonly assigned U.S. patent application Ser. No. 08/978,084 filed on Nov. 25, 1997, and U.S. Pat. No. 6,414,490, the disclosures of which are incorporated by reference herein, and in copending, commonly assigned U.S. patent application Ser. No. 09/718,946, filed on Nov. 22, 2000, the disclosure of which is also incorporated by reference herein, a magnet having poles spaced apart from one another along a horizontal axis provides a horizontally oriented magnetic field within a patient receiving gap between the poles. Such a magnet can be used with a patient positioning device including elevation and tilt mechanisms to provide extraordinary versatility in patient positioning. For example, where the patient positioning device includes a bed or similar device for supporting the patient in a recumbent position, the bed can be tilted and/or elevated so as to image the patient in essentially any position between a fully standing position and a fully recumbent position, and can be elevated so that essentially any portion of the patient's anatomy is disposed within the gap in an optimum position for imaging. As further disclosed in the aforesaid applications, the patient positioning device may include additional elements such as a platform projecting from the bed to support the patient when the bed is tilted towards a standing orientation. Still other patient supporting devices can be used in place of a bed in a system of this type. Thus, magnets of this type provide extraordinary versatility in imaging.

FIG. 1 of the current application shows a sectional view of an MRI magnet subsystem 100. MRI magnet subsystem 100 includes a magnet having a ferromagnetic frame 102, a flux generating means that is described in further detail below, and a patient handling system 106. The ferromagnetic frame 102 includes a first side wall 108 and a second side wall 110. The side walls 108 and 110 extend vertically. For purposes of clarity, FIG. 1 does not show the second side wall 110 or any of its associated structures. The ferromagnetic frame 102 also includes a top flux return member 112 and a bottom flux return member 114. The top flux return member 112 may include two substantially horizontal columns 116 and 118. Between these two columns, a top opening 120 is defined. Similarly, the bottom flux return member 114 may include two columns 122 and 124 that together define a bottom opening 126. Thus, the side walls 108 and 110 and the flux return members 112 and 114 form a rectilinear structure, with the top flux return member 112 constituting the top wall of the rectilinear structure, the bottom flux return member 114 constituting the bottom wall of the rectilinear structure and the side walls 108 and 110 forming the side walls of the rectilinear structure. The frame of the rectilinear structure defines a front patient opening 128 on one side of the frame 102 and a similar back patient opening 130 on the opposite side of the frame 102. The ferromagnetic frame 102 further includes a first magnetic pole 132 and a second magnetic pole 134. The first magnetic pole 132 extends from the first side wall 108 towards the second side wall 110 and the second magnetic pole 134 extends from the second side wall 110 towards the first side wall 108. Magnetic poles 132 and 134 are generally cylindrical and are coaxial with one another on a common horizontal polar axis 136. Between the magnetic poles 132 and 134 is a gap 131 accessed by the front patient opening 128, the back patient opening 130, the top opening 120 or the bottom opening 126. The gap 131 defines a patient-receiving space 135.

The flux generating means includes a first electromagnetic coil assembly 138 which surrounds the first magnetic pole 132, and a second electromagnet coil assembly 140 which surrounds the second magnetic pole 134. As previously noted, these electromagnetic coil assemblies 138 and 140 may be either resistive or superconductive.

The patient handling system 106 is capable of three degrees of motion or freedom. The patient handling system 106 may be termed a stand-up patient handling system, although the patient handling system 106 is not limited to standing position applications. The patient handling system 106 includes a carriage 142 mounted on rails 144. The carriage 142 may move linearly back and forth along the rails 144. The rails 144 typically do not block the bottom open space 126.

A generally horizontal pivot axis 146 is mounted on carriage 142. An elevator frame 148 is mounted to the pivot axis 146. The carriage 142 is operable to rotate the elevator frame 148 about the pivot axis 146. A patient support 150 is mounted on the elevator frame 148. The patient support 150 may be moved linearly along the elevator frame 148 by an actuator 152. Thus, a patient 154 can be positioned with a total of three degrees of freedom, or along three axes of movement. Specifically, the patient handling system 106 can move a patient 154 in two linear directions and also rotate patient 154 around an axis. The solid black arrows of FIG. 1 show the three axes of movement possible with the patient handling system 106. Note that often the rails 144 are mounted such that portions of patient 154 may be positioned below the rails 144 through bottom open space 126.

Often, a foot rest 156 may be used in order to support a patient in a standing position. Given the wide variety of positions possible with the patient handling system 108, many other such supports may be required, such as seats or straps.

The MRI magnet subsystem 100 with patient handling system 106 can be contrasted with an older MRI system such as shown in FIGS. 2A and 2B. Older MRI apparatus 200 has a magnet canopy 202 and a bed 204 on which the patient 206 lies recumbent. The bed 204 is capable only of linear motion to the left and right in the orientation of FIG. 2B. This linear motion is restricted to a horizontal plane. Thus, many of the advantages of the patient handling system as discussed in the aforementioned applications are unavailable. A control panel 208 with simple controls 210 may be mounted directly to the magnetic canopy 202. Alternatively, the control panel 208 may be mounted directly to the bed 204.

The greatly increased number of options for positioning a patient available with the patient handling system 106 allows for procedures unavailable in prior art systems. One such set of procedures involves the use of patient motion in imaging, and thus diagnosing, for example, spinal problems. Specifically, the motion of patients in weight-bearing position, commonly a sit down or stand-up position, allows magnetic resonance imaging to occur in situations in which their medical symptoms, such as pain, occur. For example, if a nerve is being pinched, the patient lying recumbent in older MRI apparatus 200 may not show these symptoms because his spine will not be demonstrating the situation that gives rise to his pain. Contrarily, the imaging of portions of the spine in either an upright, weight-bearing position, or in lateral motion from such position, can lead to more accurate imaging and diagnoses of spinal problems.

SUMMARY OF THE INVENTION

The present invention advantageously overcomes the shortcomings of the prior art by providing a method for performing magnetic resonance imaging, the method comprises the steps of positioning a patient in an upright standing position in a patient receiving space of a magnetic resonance imaging apparatus having a pair of poles and scanning the patient as the patient moves laterally. In this way the patient is desirably scanned in a position that replicates a position critical to diagnosis of an existing medical condition.

The method further desirably includes the steps of having the patient come to a fixed position during lateral movement and scanning the patient in the fixed position.

The method further desirably includes imaging the patient in a coronal scan or axial scan orientation. Both the axial scan and coronal scan orientations offer advantages over the prior art by allowing for speedy and more accurate diagnosis of painful injuries associated with the spine.

The method further desirably comprises the step of controlling the movement of the patient. By controlling the patient's movement the images obtained via the scan are more accurate and such images may be obtained more quickly. Such controls may be achieved by placing supports in a plane in front of and/or behind the patient.

Further in accordance with an aspect of the present invention, the patient may be positioned such that the patient is facing a pole face of the magnetic resonance imaging apparatus. In this way the patient is able to move laterally over an angle large enough to allow for imaging and subsequent diagnosis in a position that causes discomfort or pain to the patient.

These and other advantages may be realized in an MRI apparatus comprising a pair of pole faces that define a patient receiving space therebetween. The apparatus further desirably includes a patient support capable of supporting a patient in weight bearing position and flux generating means for acquiring images of a patient positioned in the receiving space as the patient moves laterally.

DETAILED DESCRIPTION

Figure 1:
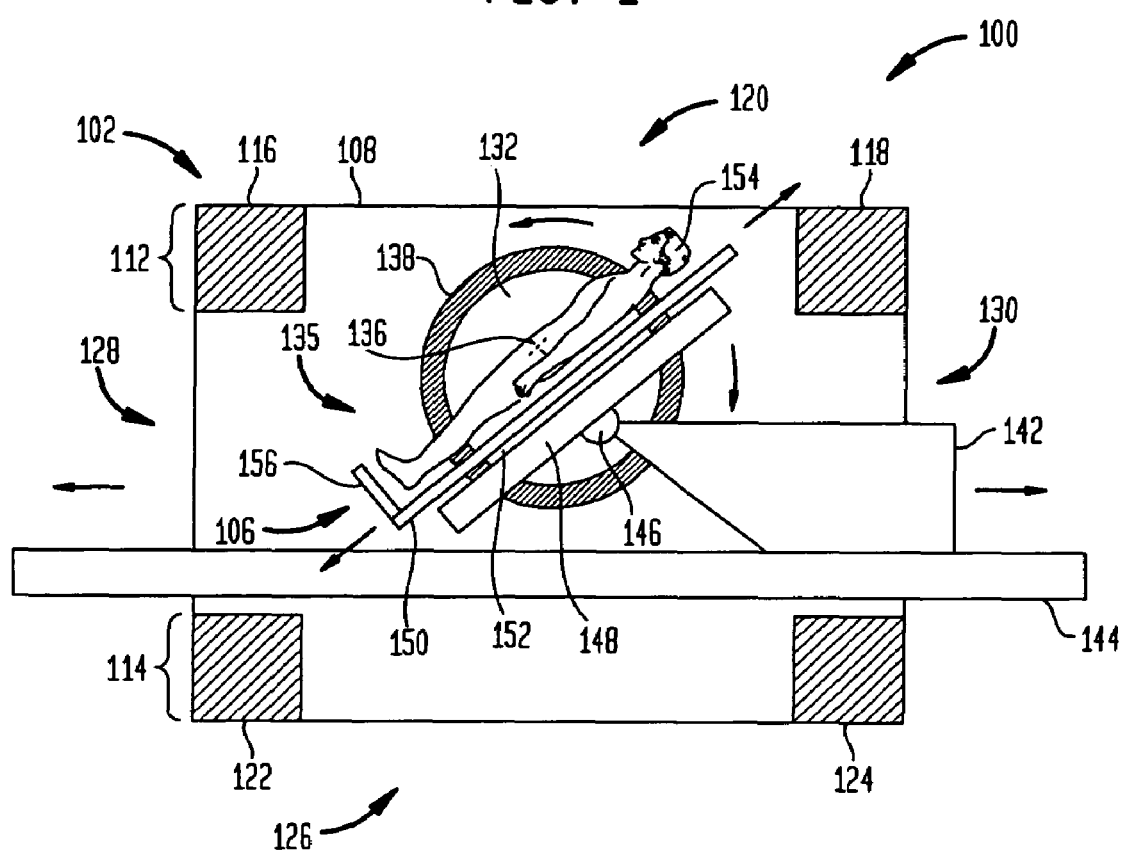
FIG. 1 is a sectional view of a schematic of an MRI apparatus in accordance with an aspect of the present invention.
Figure 2A:
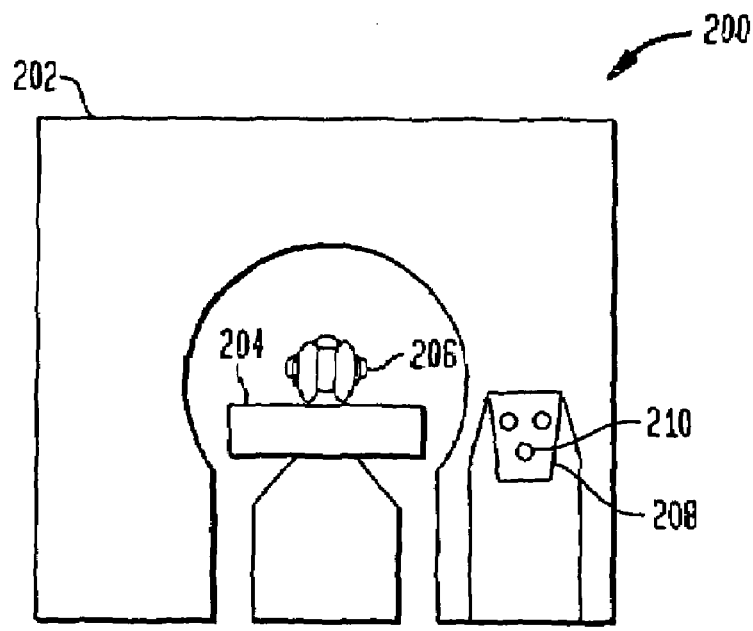
FIG. 2A is a diagrammatic frontal elevation view prior art MRI apparatus.
Figure 2B:
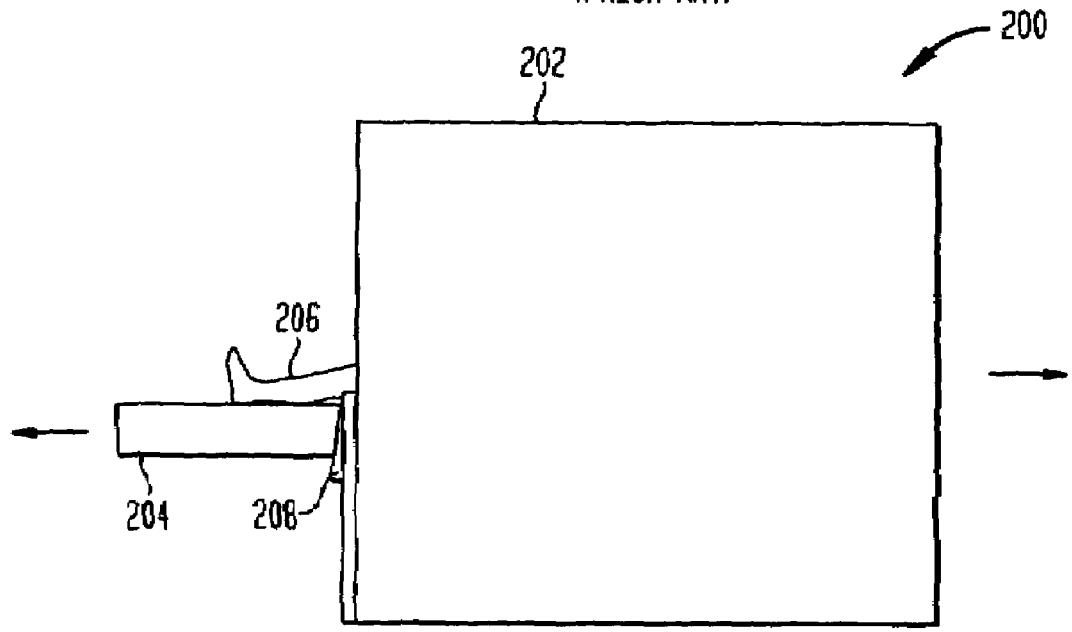
FIG. 2B is a diagrammatic side elevation view of the MRI apparatus of FIG. 2A.
Figure 3:
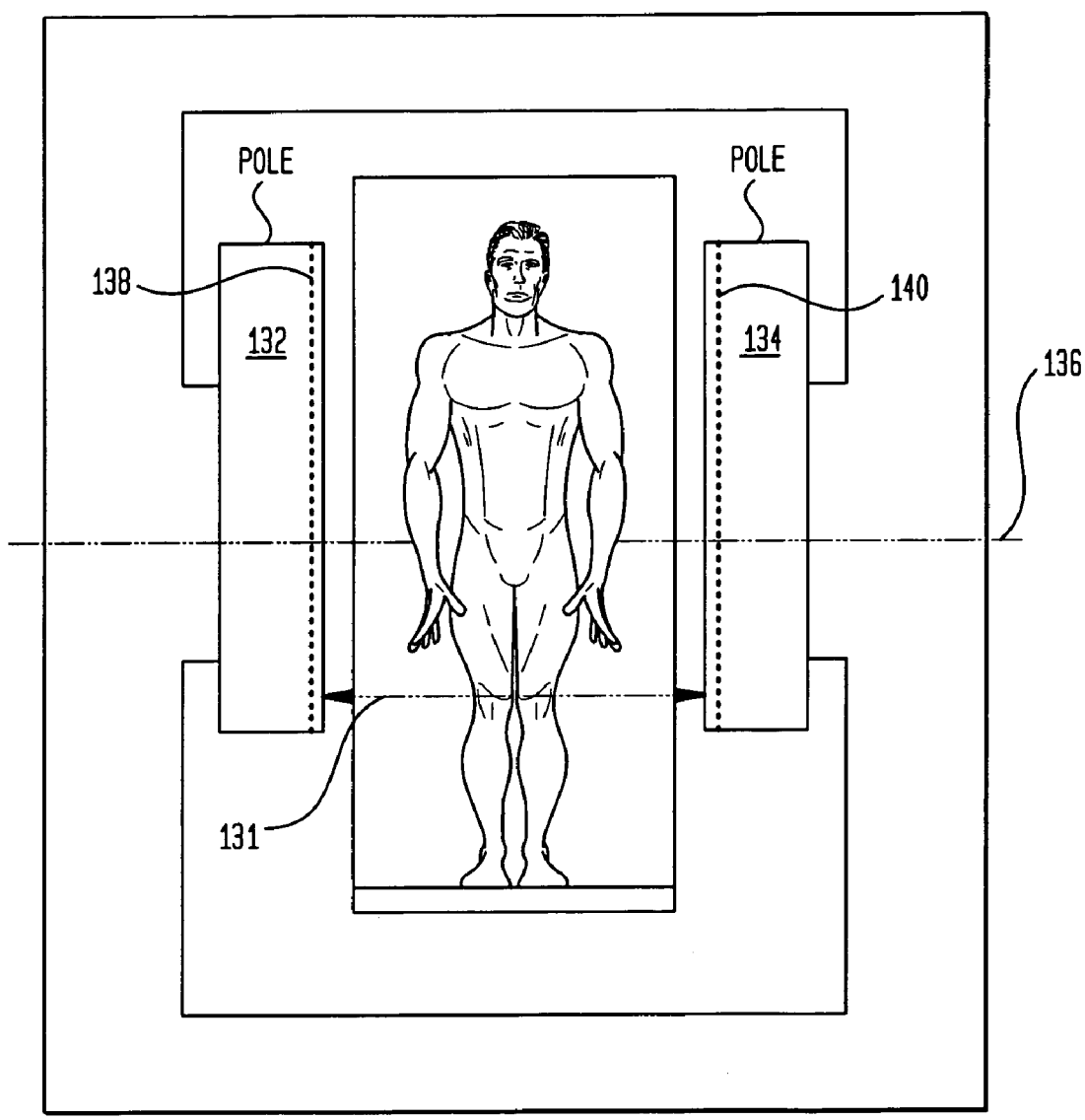
FIG. 3 is a frontal view of a patient standing in an MRI apparatus in accordance with an aspect of the present invention.
Figure 4:
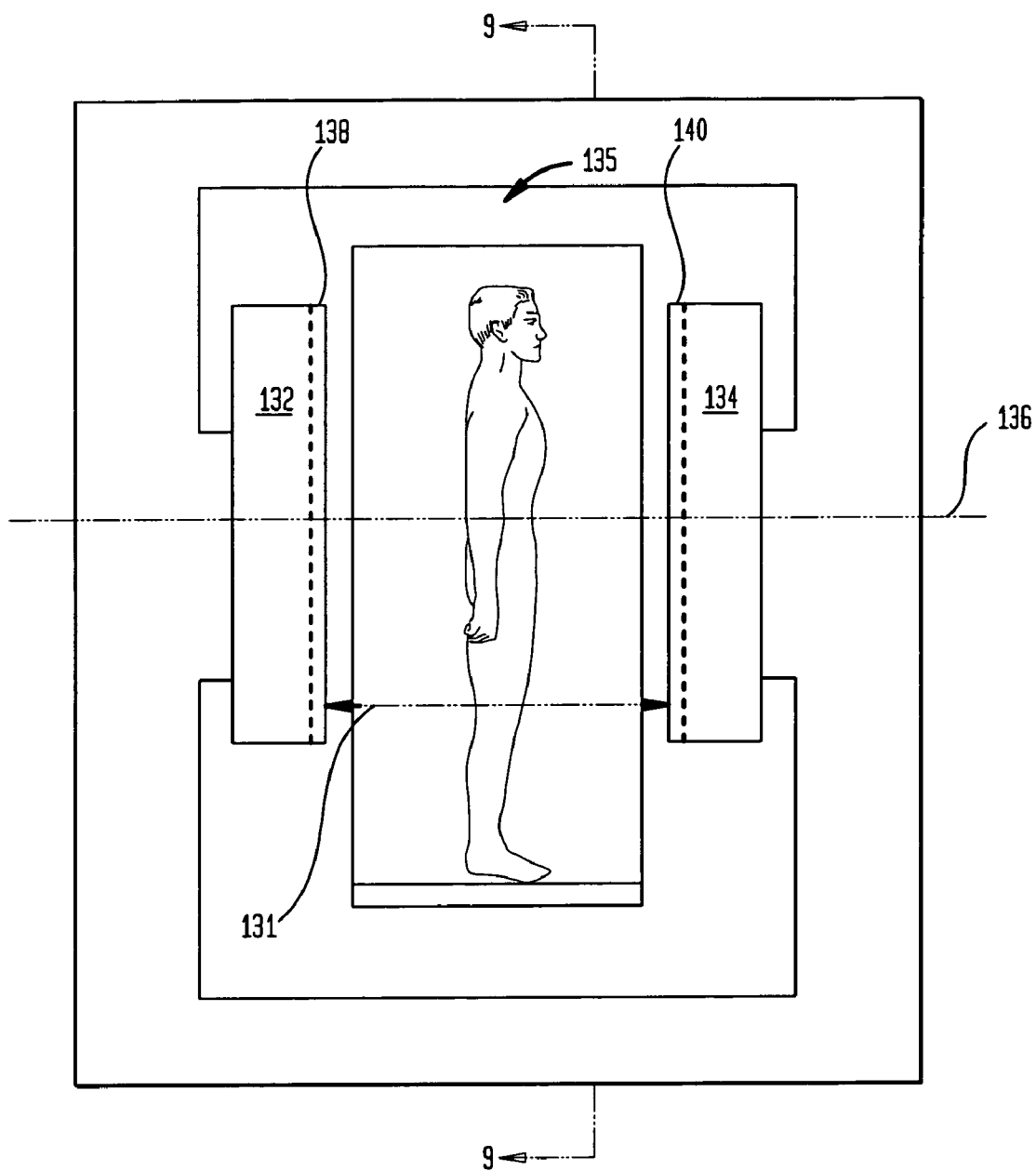
FIG. 4 is a frontal view of a patient standing in an MRI apparatus in accordance with an aspect of the present invention.

Among the various positions a patient can assume during a scan are standing while facing out of the magnet, as shown in FIG. 3, as well as standing while rotated 90 degrees from this position, thus facing one of the magnet poles, as shown in FIG. 4. This latter position is particularly advantageous for studies of the spine, including the cervical, lumbar, and thoracic spine.

Figure 5:
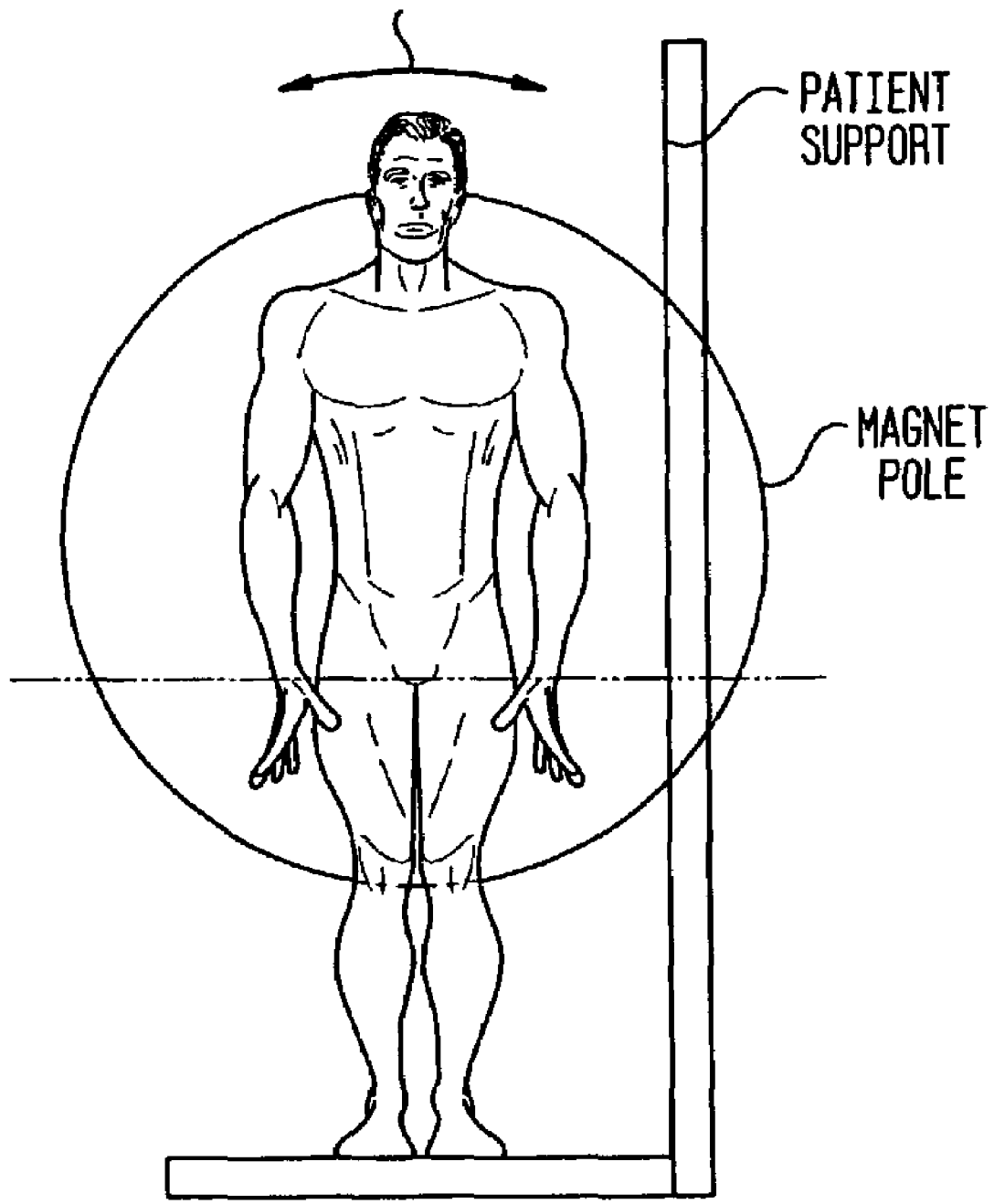
FIG. 5 is a sectional view taking along line 9-9 of FIG. 4.

FIG. 5 is a sectional view taken along line 9-9 in FIG. 4. To illustrate how this may be used, consider the following study of the lumbar spine. A patient can be positioned standing in the magnet facing one of the poles of the magnet. In this position, the patient may engage in lateral or side-to-side motion generally pivoting about the hip region of the body, as shown in FIG. 5. Images may then be taken at a series of sequential body positions along the path of this lateral motion. Here, a preferred scan orientation is coronal.

Once this series of scans is complete, they may be diagnosed or analyzed for any abnormal condition of the spine, for example as related to nerve roots, vertebrae or intervertebral disks. This diagnosis may be facilitated by use of a cine image display feature, which sequences through the images in rapid succession so as to create a movie effect. The images can also be viewed individually as still images.

An alternate procedure for obtaining lateral motion images is to choose a single lateral position rather than a series of lateral positions.

Based on the results of this study, a subsequent scan(s) will focus on a portion of the lumbar spine such as a particular disk or vertebrae or other feature of the spine which has been judged to be problematic based on the results of the lateral motion scan. Here, a different scan orientation may be chosen such as axial, which is widely used for diagnostic studies of the spine. Regarding patient orientation, this next scan may be performed with the patient in either a vertical orientation, or one or more of the lateral positions examined in the previous scan.

Scanning protocols found to be particularly useful in performing such studies include driven equilibrium scanning and generalized oblique positioning of the image planes.

Figure 6:
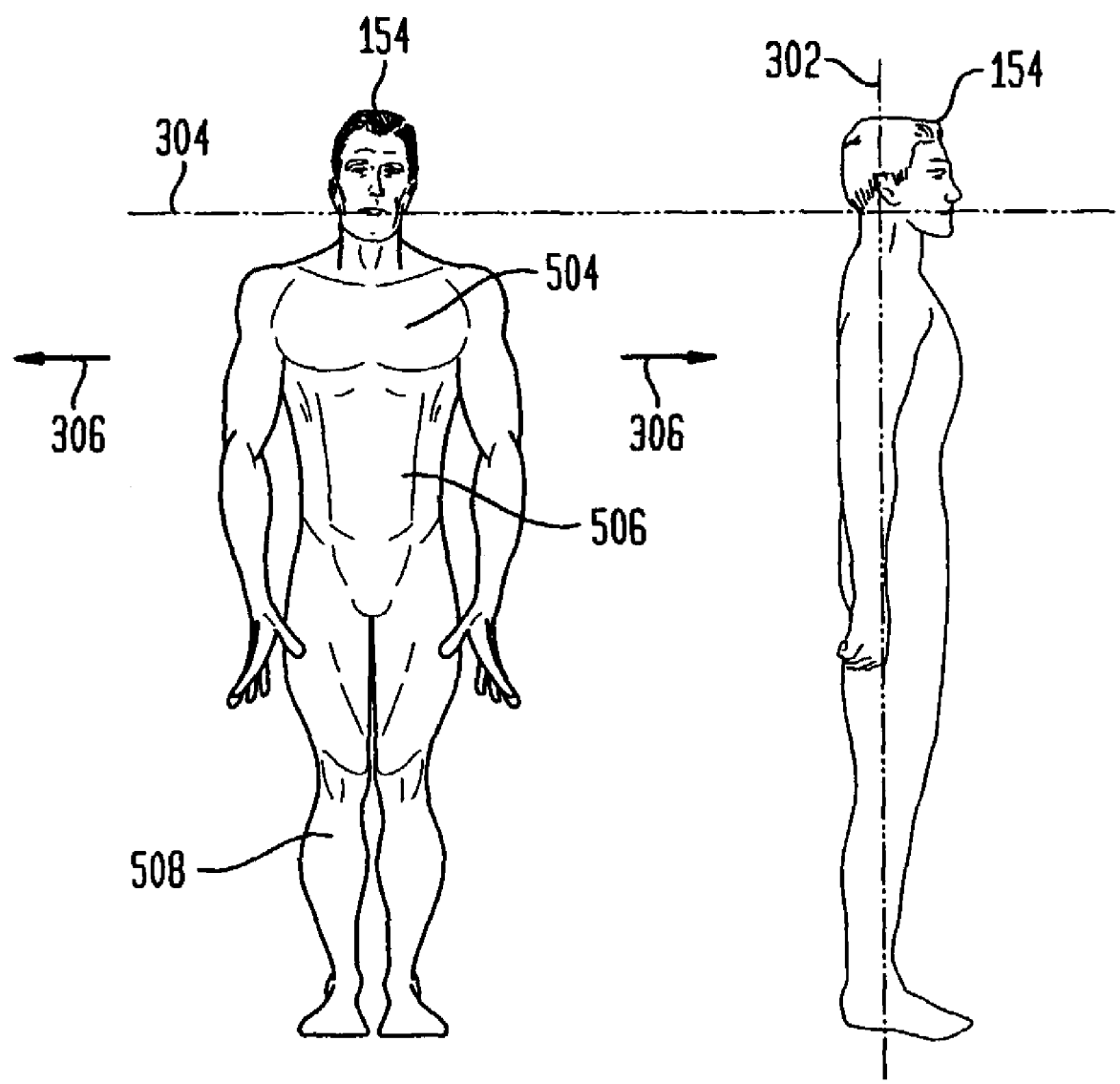
FIG. 6 illustrates orientations of a standing patient in accordance with the present invention.

FIG. 6 further illustrates the potential orientations of a standing patient 154. The frontal plane 302 may be defined as a vertical plane from head to foot and parallel to the shoulders. The axial plane 304 may be defined as a horizontal plane perpendicular to the frontal plane. The lateral direction 306 is a direction to either the right or left side of the patient, in general parallel to, the frontal plane. FIG. 6 thus gives the fundamental orientation of the patient 154.

Figure 7:
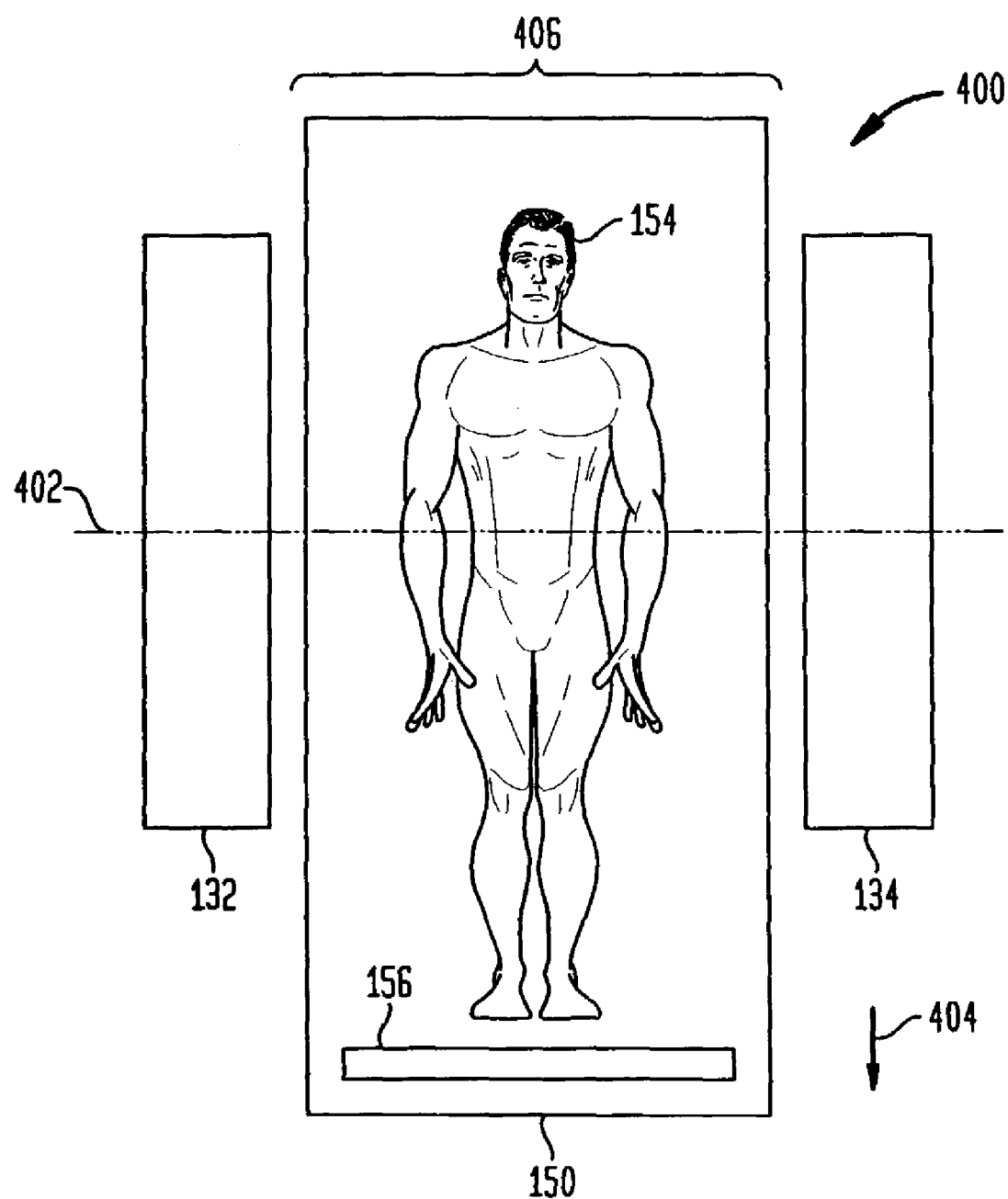
FIG. 7 is a frontal view of a patient in an MRI apparatus in accordance with an aspect of the present invention.

FIG. 7 is a frontal elevation schematic view of MRI magnet subsystem 100. In a particular configuration 400, patient support 150 is in a vertical position. Dotted line 402 represents the generally horizontal pole axis which is defined by the center of the face of magnetic pole 132 and the center of the face of magnetic pole 134. In configuration 400, the patient 154 has a frontal plane 302 parallel to the pole axis 402. Vector 404 shows the presence of gravity affecting patient 154. Gravity vector 404 causes a load upon the spinal system of the patient 154. Note that the width 406 of the pole gap 131 between the poles 132 and 134 may be only slightly wider than the width of the shoulders of some patient 154. While the configuration 400 may show some spinal problems and pain due to gravitational load on the spinal system not shown in the recumbent position of an older MRI apparatus, such as apparatus 200, many symptoms only express themselves in particular positions. While MRI apparatus 100 has a patient handling system 106 capable of three degrees of movement which may place the patient in almost any position in a plane perpendicular to the pole axis 402, equidistant from the faces of pole magnets 132 and 134, many spinal problems will only show their symptoms when in positions where the spine is not aligned. In other words, spinal problems often show symptoms, such as pain, in a different position. However, because the width 406 of the pole gap 131 between the poles 132 and 134 may be limited in current implementations of MRI magnet subsystem 100, a new procedure is required in order to exploit potential diagnostic capabilities.

Figure 8:
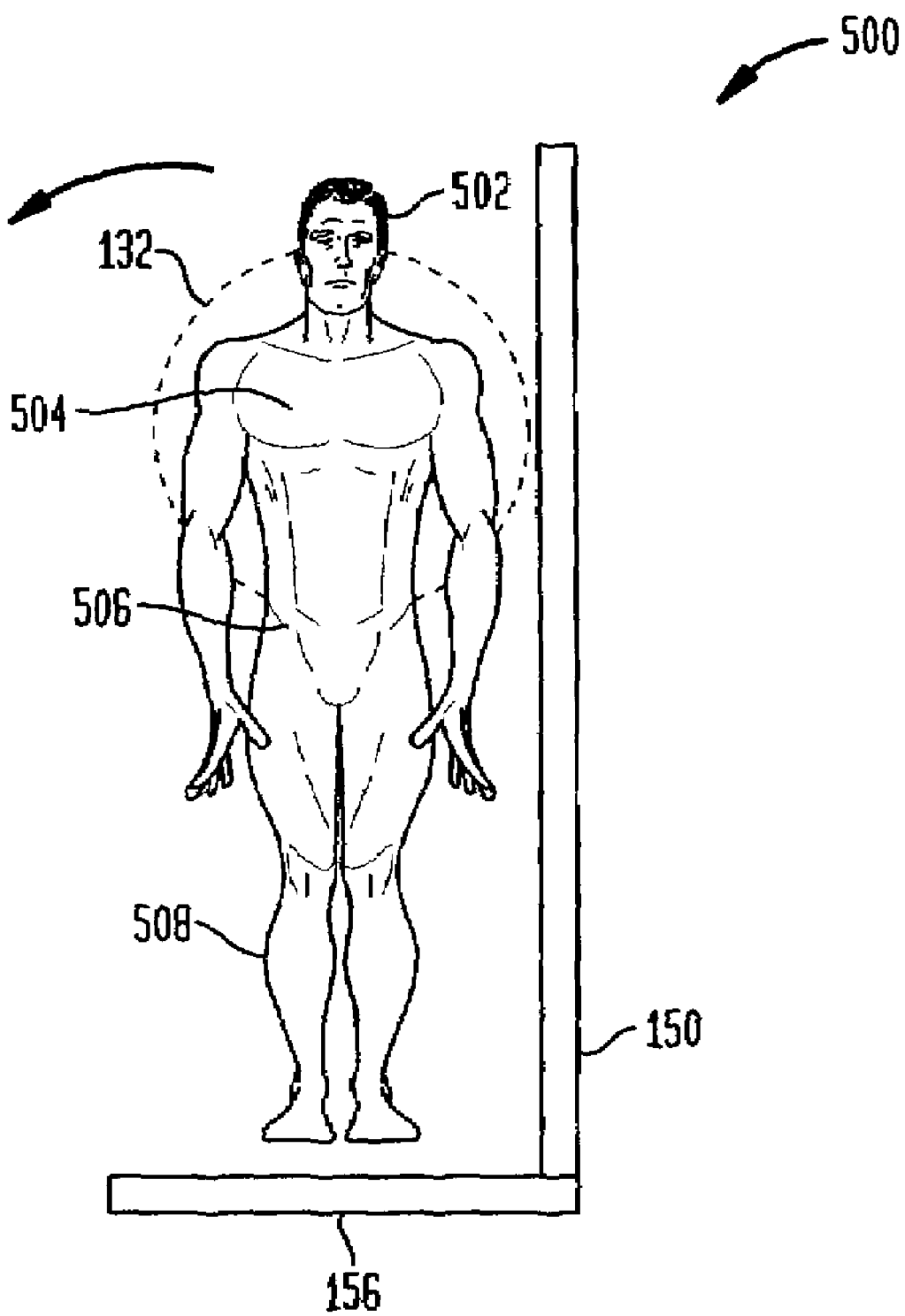
FIG. 8 is a sectional view of a patient in an MRI apparatus in accordance with an aspect of the present invention.

FIG. 8 is an elevated schematic side view of MRI magnet subsystem 100 with MRI magnet subsystem 100 and patient 154 in a particular configuration 500. In configuration 500, patient 154 has a frontal plane, which is perpendicular to the horizontal pole axis 402. As in FIG. 7, in configuration 500 patient 154 is standing on a foot rest 156. Thus, the patient 154 will be facing magnetic pole 132 or magnetic pole 134. The patient 154 may then move a part of his body laterally. The part of his body that should be moved laterally depends upon which section of the spine is under investigation. The spine is generally divided into three sections for diagnostic investigation. These sections are the cervical spine, the thoracic spine, and the lumbar spine. Patient 154 has a head 502, a torso 504 and an abdomen 506. If the cervical spine is under investigation, the patient will laterally move his head 502, by, for example, tilting his head 502 away from the patient support 150. As the patient 154 tilts his head 502 away from patient support 150, the cervical spine will bend. The MRI main apparatus 100 will take a full series of images, probably involving many images per second. Presumably, one of the positions taken by the cervical spine will be the position that is causing patient 154 pain. Alternatively, to save time and cost, the patient could move his head only to the position that causes him pain, and this could receive a full imaging protocol. Similarly, if the thoracic spine is under investigation, patient 154 would move his torso 504 laterally away from patient support 150, while attempting to keep his abdomen 506 and legs 508 straight. Again, the MRI main apparatus 100 can take a large series of images as the patient moves his torso laterally, thus capturing the movement of the thoracic spine. Among the positions imaged of the thoracic spine of patient 154 will be the position causing the pain or exhibiting the symptoms that are being investigated in patient 154. Again, alternatively, to save time and cost, the patient could laterally move his torso only to the position that causes him pain or exhibits the symptoms, and this lateral position could receive a full imaging protocol. If the lumbar spine is under diagnostic investigation for pain or other symptoms, the patient 154 in configuration 500 will move laterally away from patient support 150, while attempting to keep his legs 508 straight. The lumbar vertebrae of the lumbar spine will go through a series of positions, and the MRI main apparatus 100 will take a large series of images of the lumbar vertebrae in the series of positions. At least one of the positions assumed by patient 154 moving laterally will be the one that exhibits pain or other symptoms in the lumbar spine. Again, to save time and cost, the patient could assume the position that causes him pain or exhibits the symptoms, and this position could receive a full imaging protocol. In each of these imaging cases, it may be advantageous to image the patient in at least one non-painful or non-symptomatic position for purposes of comparison.

In another embodiment, the imaging of the lateral motion of patient 154 is performed with a coronal scan orientation. A coronal scan orientation is one in which the image plane is parallel to the frontal plane 302 of the patient 154. However, alternative scan orientations are possible and may in some situations, be preferable. Given the technique of generalized oblique positioning of an image plane, in which image planes can assume any arbitrary orientation, it may be advantageous to assume special scan orientations for specific orientation of the lateral movement of patient 154.

After the results of the lateral motion scans are analyzed, certain specific portions within the studied section of spine will be of particular interest. For example, in the case of a pinched nerve, the original lateral motion scans of the thoracic spine may show the nerve being pinched, but now a focus on the nerve is beneficial. Often, an axial scan orientation true to the anatomy is advantageous to diagnostic imaging of the spine. The patient may remain with the spine aligned in a vertical orientation, or the patient may assume one of the lateral positions that he assumed in the previous lateral movement scans. Either or both would be advantageous.

The use of an axial scan orientation is beneficial as the plane resolution of an image plane is higher than the resolution of the slice thickness in two dimensional imaging as discussed above. Thus, to obtain better resolution of the vertebrae and nerves of interest, a different orientation is advantageous. Note, techniques that can generate isometric voxels, such as three dimensional scanning, exist. However, such scanning techniques have other limitations.

Figure 9:
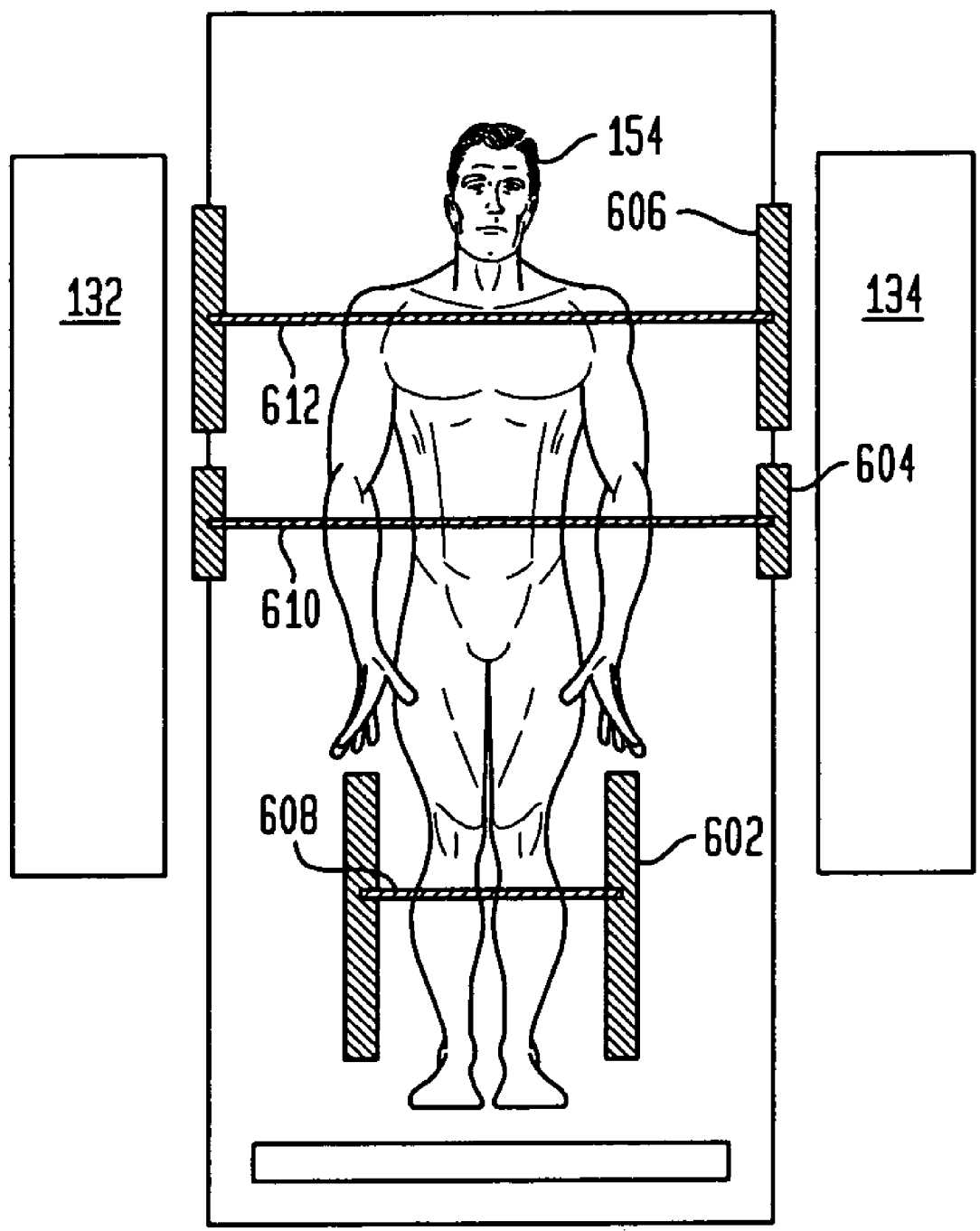
FIG. 9 illustrates a patient standing in an MRI apparatus sin accordance with another aspect of the present invention.

FIG. 9 shows supports that may be advantageous to scanning of the patient 154 during the lateral motion needed in the above procedures. Such supports are described in commonly assigned U.S. patent application Ser. No. 10/126,015, the disclosure of which is incorporated by reference herein in its entirety. Each support may be used to restrict a patient's motion in a direction perpendicular to the direction of lateral motion during lateral motion. In general, the bars advantageously allow for restriction of select regions of the human anatomy during scanning. For example, the bars may be placed between the knees and ankles to restrict motion during lateral motion study. In addition, bars may be placed at each side of a patient's waist to restrict lateral motion thereof during scanning of the lumbar area. In other words, the bars may serve as anchor points. The bars may also be used to define the range of motion during scanning. The bars may also be used as patient immobilizing supports.

In particular, leg support 602, which includes leg bar 608, may be placed at a position slightly in front of a patient's legs to limit motion of the patient's feet and legs in a direction perpendicular to the direction of lateral motion 306 and hold the patient still during imaging. The abdominal support 604 may perform a similar function as leg support 602 for the patient's abdomen by restricting forward abdominal motion. Thoracic support 606 may be used similarly to hold the patient's torso in the frontal plane. These supports used singularly or together may assist patient 154 in maintaining a portion of a patient's body in the correct plane when performing lateral motion. As FIG. 9 further shows abdominal support 604 comprises abdomen bar 610 while thoracic support 606 includes thoracic bar 612. If the patient 154 is having a diagnostic study of his lumbar spine, leg bar 608 will keep his legs 608 in position while his abdomen 506, torso 504 and head 502 all move laterally. If the patient 154 is having a diagnostic study of his thoracic vertebrae, the abdominal bar 610 may be added to keep his leg 508 and abdomen 506 straight while allowing his torso 504 and head 502 to laterally move. Finally, if patient 154 is undergoing a diagnostic study of his cervical spine, thoracic bar 612 may be added. Thus, the patient's legs 508, abdomen 506 and torso 504 are all held in axial position while the head 502 undergoes lateral movement. All of these assist in the patient 154 isolating lateral movement in the section of spine which is to be studied. In the current implementation of MRI apparatus 100, the gap between magnetic poles 132 and 134 is insufficient to have the patient 154 in a sitting position with his frontal plane perpendicular to the horizontal pole axis. However, alternative embodiments of MRI magnet subsystem 100 may allow an increased pole gap between magnetic poles 132 and 134. In such a case, it may be advantageous for the patient 154 to perform the various lateral movements discussed hereinabove, from a sitting position, utilizing the appropriate supports.

As noted above, MRI apparatus 100 is capable of generalized oblique positioning of the image planes. Thus, as scan orientation is arbitrary in any dimension, it is possible that certain scan orientations beyond the coronal and axial orientations discussed may be advantageous. For example, as previously discussed, a detailed study of the nerves by an axial scan orientation is possible. If such a study is done with the patient's spine in a lateral position, it may be advantageous to image the first vertebrae in an axial orientation with respect to that vertebrae, and to image the second vertebrae in an axial orientation with respect to that second vertebrae. These first and second scan orientations will define axial imaging planes at an angle from each other. However, this may be advantageous. As radiologists and other diagnosticians explore this very flexible tool, other advantageous scan orientations for lateral movement studies and lateral position studies will become apparent. Also, other standard scanning protocols such as driven equilibrium fast spin echo scanning may be advantageous in performing such load bearing lateral motion lateral position studies.

FIG. 7 demonstrates that the gap 406 of an MRI magnet subsystem 100 may prevent the lateral motion necessary to bend the thoracic or lumbar spine of a patient when the frontal plane of the patient 154 is parallel to the pole axis 402. However, the cervical spine may be bent by lateral movement of the head despite the gap 406. Thus the advantages of diagnostic imaging of the cervical spine in lateral positions or movement against gravity may be obtained without loading the patient 154 in a position with the frontal plane 302

Rotation of the spine at the cervical spine, the thoracic spine, or the lumbar spine may cause the expression of symptoms such as pain only when the spine of patient 154 is under load. Thus, in additional to lateral movement, a patient may be rotated using one of three degrees of motion made available via patient handling system 106. This will allow a special diagnostic procedure involving spinal positions or motion under gravitational load. Thus, differences that may occur between weight hearing and other positions may further enhance diagnosis.

MRI systems capable of imaging patients while essentially vertically oriented, that is standing or sitting for example, provide significant advantages over recumbent-only patient positioning capable MRI systems. One major advantage is the ability to image patients in a weight-bearing position, which is more closely related to their position of symptoms or pain. Another major advantage is the ability to determine and control the position of the patient in three dimensions. This latter capability is enabled by the open architecture of the magnet design providing ample space for patient positioning, and the versatile patient positioning system, which independently of the orientation of the patient during the scanning procedure, can move the patient vertically, horizontally and rotationally.

The complete study described above in the weight-bearing condition of the patient demonstrates the increased diagnostic capability made possible by the ability to control the position of a patient in three dimensions.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for performing magnetic resonance imaging, the method comprising the steps of:
   establishing a static horizontal magnetic field between a pair of opposed pole faces along a horizontal field axis of a magnetic resonance imaging apparatus, the opposed pole faces being spaced apart along the horizontal field axis to define a patient receiving gap;
   positioning a patient with the spine in a weight bearing position on a patient support apparatus within the patient receiving gap of the magnetic resonance imaging apparatus such that a frontal plane of the patient is perpendicular to the horizontal field axis with the patient positioned to face one of the pole faces;
   scanning a first portion of the spine as the patient's torso moves laterally between a plurality of imaging positions;
   adjusting the position of the patient support such that a second portion of the spine can be scanned; and
   scanning the second portion of the spine as the patient's torso moves laterally between a plurality of imaging positions.

2. The method as claimed in claim 1 further comprising the steps of having the patient come to a fixed position during said lateral movement and scanning the patient in said fixed position.

3. The method of claim 1 wherein said step of scanning further comprises scanning the patient in a coronal scan orientation.

4. The method of claim 1 further comprising viewing the result of said scanning as a still image.

5. The method of claim 1 wherein the first portion of the spine comprises the lumbar spine and the second portion of the spine comprises the thoracic spine.

6. The method of claim 1 wherein the first portion of the spine comprises the thoracic spine and the second portion of the spine comprises the cervical spine.

7. The method of claim 1 wherein the step of adjusting comprises translating the patient support apparatus along a direction substantially perpendicular to the horizontal field axis.

8. The method of claim 1, further comprising:
   positioning the patient in a supine position on the patient support apparatus within the patient receiving gap of the magnetic resonance imaging apparatus; and
   scanning the first portion of the patient's spine as the patient's torso moves laterally between a plurality of imaging positions, so that the scanned images in such position may be used as a reference.

9. The method of claim 1, wherein the step of positioning the patient is performed by operating the patient support apparatus to move vertically, horizontally, or rotationally.

10. The method of claim 1 wherein said step of scanning further comprises scanning the patient in an axial scan orientation.

11. The method of claim 10 further comprising the step of scanning the patient in a fixed lateral position.

12. The method of claim 1 further comprising the step of controlling the movement of the patient.

13. The method of claim 12 wherein said step of controlling further comprises the step of placing a bar between the patient's knees and ankles.

14. The method of claim 12 wherein said step of controlling further comprises the step of placing a bar at a side of the patient's waist.

15. The method of claim 12 wherein said step of controlling further comprises the step of defining the patient's range motion during scanning using a bar placed within the patient receiving gap.

16. A method for performing magnetic resonance imaging of the spine in a weight-bearing condition, the method comprising the steps of:
   establishing a static horizontal magnetic field between a pair of opposed pole faces along a horizontal field axis of a magnetic resonance imaging apparatus, the opposed pole faces being spaced apart along the horizontal field axis to define a patient receiving gap;
   positioning a patient with the spine in a weight-bearing position on a patient support apparatus capable of elevating and rotating the patient within the patient receiving gap of the magnetic resonance imaging apparatus such that a longitudinal axis of the patient coincident with the spine is positioned in the imaging volume of the magnet gap;
   scanning a first portion of the spine at a first position;
   moving the patient laterally among a plurality of imaging positions by pivoting the lateral motion around a longitudinal position aligned within the spine; and
   scanning the first portion of the spine of the patient in at least one other lateral position.

17. The method of claim 16 wherein the first portion of the spine comprises the lumbar spine.

18. The method of claim 16 wherein the first portion of the anatomy of the patient comprises the cervical spine.

19. The method of claim 16 wherein the first portion of the anatomy of the patient comprises the thoracic spine.

20. The method of claim 16, wherein the weight bearing position is an upright position.

21. The method of claim 20 further comprising rotating the position of the patient support to bring the patient to a second position different than the upright position; and scanning the first portion of the anatomy of the patient in the second position.

* * * * *